United States Patent [19]  [11] 4,186,265
Davis et al.  [45] Jan. 29, 1980

[54] SEPARATION OF A TRIS(ALKYLAMINO)-S-TRIAZINE BY-PRODUCT FROM CHLORO-BIS(ALKYLAMINO)-S-TRIAZINES

[75] Inventors: Jay P. Davis, Greensboro, N.C.; Henry C. Grace; James B. Nabors, both of Baton Rouge, La.

[73] Assignee: Ciba-Geigy Corporation, Ardsley, N.Y.

[21] Appl. No.: 971,574

[22] Filed: Dec. 20, 1978

[51] Int. Cl.$^2$ .......................... C07D 251/50
[52] U.S. Cl. ........................ 544/204; 544/208
[58] Field of Search ........................ 544/204, 208

[56] References Cited

U.S. PATENT DOCUMENTS

| | | | |
|---|---|---|---|
| 3,681,337 | 8/1972 | Petree | 544/204 |
| 3,919,222 | 11/1975 | Eichenberger et al. | 544/204 |

*Primary Examiner*—John M. Ford
*Attorney, Agent, or Firm*—Karl F. Jorda

[57] ABSTRACT

A method is provided for separating tris(alkylamino)-s-triazine by-product from chloro-bis(alkylamino)-s-triazines by extracting tris(alkylamino)-s-triazine from an organic solution containing a mixture of tris(alkylamino)-s-triazine and chlorobis(alkylamino)-s-triazine with an aqueous acid solution in the pH-range of 5.4–0.5 and according to a further embodiment of the present invention, treating an alkaline aqueous effluent containing a mixture of chloro-bis(alkylamino)-s-triazine and tris(alkylamino)-s-triazine with an agent capable of reducing the pH value below 5.4 and extracting the chloro-bis(alkylamino)-s-triazine with a water immiscible solvent, the tris(alkylamino)-s-triazine remaining in the aqueous phase.

10 Claims, No Drawings

SEPARATION OF A TRIS(ALKYLAMINO)-S-TRIAZINE BY-PRODUCT FROM CHLORO-BIS(ALKYLAMINO)-S-TRIAZINES

BACKGROUND OF THE INVENTION

1. Field of the Invention

Chloro-bis(alkylamino)-s-triazine compounds having the following structural formula

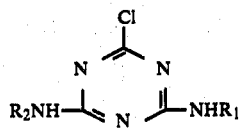

in which $R_1$ and $R_2$ independently represent lower alkyl or cycloalkyl, inhibit the growth of plants and are widely used as herbicides. Especially valuable as herbicides are atrazine(2-chloro-4-ethylamino-6-isopropylamino-s-triazine), simazine (2-chloro-4,6-bis(ethylamino)-s-triazine), and propazine(2-chloro-4,6-bis-(isopropylamino)-s-triazine). These compounds are employed both as selective herbicides for weed control among cultivated plants and as soil sterilants for the total elimination of undesired plant growth. Further details with respect to these and other chloro-bis(alkylamino)-s-triazines are set forth in U.S. Pat. No. 2,891,855.

2. Description of the Prior Art

In the process for production of chloro-bis(alkylamino)-s-triazine compounds of the structural formula (I), as defined above, a process stream is obtained comprising a compound as defined by structural formula (I) together with large amounts of undesired tris-(alkylamino)-s-triazine by-products as impurities. In order to remove these impurities large amounts of water are employed.

This has resulted in creating a large amount of aqueous alkaline effluent containing a large variety of triazine impurities, including tris(alkylamino)-s-triazines and also a compound of the above structural formula (I), for instance, 2-chloro-4-ethylamino-6-isopropylamino-s-triazine. Thus, prior to the present invention an extractive technique which would allow separation of tris(alkylamino)-s-triazine and chloro-bis-(alkylamino)-s-triazine had been highly desired but was unavailable.

U.S. Pat. No. 3,681,335 purports to teach a method for the suppression of tris(alkylamino)-s-triazine in the production of chloro-bis(alkylamino)-s-triazine through adjustment of pH, but this method is not only not being practiced because of the risk of hydrolysis losses but also is basically different because it involves prevention of formation of tris(alkylamino)-s-triazine compounds by immediate removal of any excess alkylamine reactant.

DETAILED DISCLOSURE

In accordance with the present invention an organic water-immiscible process stream which is obtained in the production of a chloro-bis(alkylamino)-s-triazine compound having the following structural formula

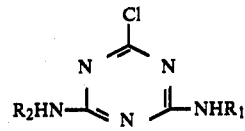

in which $R_1$ and $R_2$ independently represent lower alkyl of 1 to 4 carbon atoms, such as methyl, ethyl, isopropyl, n-butyl, sec-butyl tert.-butyl or cycloalkyl of 3 to 6 ring carbon atoms, such as cyclopropyl, cyclopentyl, cyclohexyl, and which contains a tris(alkylamino)-s-triazine by-product of the structural formula

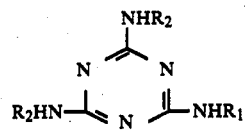

wherein $R_1$ and $R_2$ have the meaning defined under structural formula (I), is extracted with a dilute aqueous acid of pH 0.5 to 5.4 to remove the undesirable tris(alkylamino)-s-triazine by-product from the organic layer, thus separating it from the product chloro-bis(alkylamino)-s-triazine.

Surprisingly, it has now been found that the compound of structural formula (II) is much more readily soluble in water at a pH-range from 5.4 to 0.5 than the compound of structural formula (I). A tris(alkylamino)-s-triazine compound of the structural formula (II) is, for instance, 2,4,6-tris(ethylamino)-s-triazine, 2,4,6-tris(isopropylamino)-s-triazine or 2,4-bis(ethylamino)-6-isopropylamino-s-triazine.

Thus, according to the process of the present invention a tris(alkylamino)-s-triazine by-product as defined by formula (II) can be separated from the organic process stream to a high degree, leaving all of the chloro-bis(alkylamino)-s-triazine product in the organic process stream in a purified state and essentially free of an undesirable compound of the structural formula (II).

An agent capable of providing a pH 0.5–5.4 aqueous extraction medium is, for instance, an acid such as hydrochloric acid, sulfuric acid or phosphoric acid, or a sulphonic acid, e.g., an alkyl sulphonic acid such as methanesulphonic acid, or an optionally substituted arylsulphonic acid such as, for instance, a phenylsulphonic acid unsubstituted or substituted by alkyl, halogen and/or nitro groups, for instance, phenylsulphonic acid, p-methylphenylsulphonic acid, p-chlorophenylsulphonic acid, 2- or 4-nitrophenylsulphonic acid or 2-chloro-4-nitrophenylsulphonic acid.

The water-immiscible, organic process stream is based upon a water-immiscible solvent such as, for instance, chloro-substituted aliphatic hydrocarbons such as carbon tetrachloride or ethylene dichloride, or cycloaliphatic hydrocarbons having five to seven carbon atoms, cyclohexane for instance, or aromatic hydrocarbons such as benzene or lower alkyl- or halogen- or nitro-substituted benzene, e.g., toluene, xylene, chlorobenzene, or nitrobenzene.

Under the conditions of the presently improved process according to the invention a tris(alkylamino)-s-triazine of the structural formula (II) is effectively converted to the acid salt and extracted into the aqueous phase separating it from a chloro-bis(alkylamino)-s-triazine of structural formula (I) in a water-immiscible solvent, particularly 2-chloro-4-ethylamino-6-isopropylamino-s-triazine in toluene.

A particularly preferred mode for carrying out the process according to the present inventive concept comprises the extraction of the toluene process stream obtained in the production of 2-chloro-4-ethylamino-6-isopropylamino-s-triazine with an aqueous stream rendered acidic within a pH-range of 5.4–0.5 by means of hydrochloric acid or sulfuric acid.

While the improved extraction process finds its greatest utility in the removal of the tris(alkylamino)-s-triazine impurity from an organic solution of a chloro-bis-(alkylamino)-s-triazine, it is also possible to employ the same inventive concept to effect a selective removal of a chloro-bis(alkylamino)-s-triazine from a tris(alkylamino)-s-triazine containing aqueous effluent stream. Thus, according to a further embodiment of the present invention the alkaline effluent filtrate which is obtained in the production of a chloro-bis(alkylamino)-s-triazine compound having the structural formula (I), as defined above, is treated with an agent capable of reducing the alkaline filtrate to a pH value below 5.4 followed by subjecting the thus-adjusted filtrate to an extraction treatment with a water-immiscible solvent to remove the corresponding 2-chloro-bis(alkylamino)-s-triazine compound from the filtrate.

Surprisingly, it has now been found that a tris(alkylamino)-s-triazine by-product of the structural formula (II), as defined above, is less extractible at low pH than a chloro-bis(alkylamino)-s-triazine compound of the formula (I).

Thus, according to this further embodiment of the present invention a chloro-bis(alkylamino)-s-triazine as defined by formula (I) can be removed from the alkaline effluent filtrate to a high degree which renders possible the separation of this compound in a very pure state from tris(alkylamino)-s-triazine of structure (II), which remains in the aqueous effluent.

Under the conditions of this further embodiment of the presently improved process a chloro-bis(alkylamino)-s-triazine of the structural formula (I) —2-chloro-4-ethylamino-6-isopropylamino-s-triazine in particular—is effectively extracted into the solvent whereas a tris-alkylamino-s-triazine by-product of the structural formula (II) is converted to the acid state and is not extracted by the solvent.

A preferred mode for carrying out this embodiment according to the present inventive concept comprises using the alkaline effluent filtrate which is obtained in the production of a compound of the structural formula (I), e.g., 2-chloro-4,6-bis-(ethylamino)-s-triazine, 2-chloro-4,6-bis(isopropylamino)-s-triazine or 2-chloro-4-ethylamino-6-isopropylamino-s-triazine, said alkaline effluent filtrate being rendered acid within a pH range of 5.4–0.5 by means of hydrochloric acid sulfuric acid or phosphoric acid and subjecting said acid-adjusted filtrate to an extraction treatment with a water-immiscible solvent such as xylene or particularly toluene.

A particularly preferred mode for carrying out this embodiment comprises using the alkaline effluent filtrate which is obtained in the production of 2-chloro-4-ethylamino-6-isopropylamino-s-triazine, said alkaline effluent filtrate being rendered acidic within a pH-range of 5.4–0.5 by means of hydrochloric acid or sulfuric acid and subjecting said acid-adjusted filtrate to an extraction treatment with toluene.

The following examples will serve to illustrate the improved process of the present invention. The temperatures are given in degrees centigrade.

EXAMPLE 1

To a 2-liter 3-neck flask equipped with a heating mantle, stirrer, condenser and thermometer was charged 206.9 grams of wet cake comprising essentially 58 percent of atrazine and 41 percent water, 880 grams of toluene and 0.7 grams of 2,4-bis(ethylamino)-6-isopropylamino-s-triazine (hereinafter designated as tris-compound). Stirring was begun and the mixture was heated to 85° C. When all the solids were dissolved, a small sample of the organic layer was removed. Then 610 grams of 1.09% hydrochloric acid was charged to the flask. This mixture was held with stirring at 85° for 30 minutes. Stirring was then stopped, and a sample of the organic layer was again removed. Both samples were evaporated to dryness and then analyzed for tris content. The sample prior to acid extraction contained 0.58% tris compound and the sample after extraction contained 0.08% tris compound (83% tris compound removed).

EXAMPLE 2

The process of Example 1 was repeated except that 248.5 grams of 0.40% hydrochloric acid solution was charged to the flask in place of the original acid charge. The sample prior to extraction contained 0.46% tris compound and the sample after extraction contained 0.17% tris compound (63% tris compound removed).

EXAMPLE 3

The process of Example 1 was repeated except that 163.1 grams of 0.15% hydrochloric acid solution was charged to the flask in place of the original acid charge. The sample prior to the extraction contained 0.58% tris compound and the sample after extraction contained 0.28% tris compound (47% tris compound removed).

EXAMPLE 4

The process of Example 1 was repeated except that 115.2 grams of 0.87 hydrochloric acid solution was charged to the flask in place of the original acid charge. The sample prior to extraction contained 0.46% tris compound and the sample after extraction contained 0.31% tris compound (33% tris compound removed).

EXAMPLE 5

The process of Example 1 was repeated except that 15.2% grams of 6.6% sulfuric acid was charged to the flask in place of the original acid charge. The sample prior to extraction contained 0.58% tris compound and the sample after extraction contained 0.40% tris compound (31% tris compound removed).

EXAMPLE 6

To a 2-liter 3-neck flask equipped with a heating mantle, stirrer, condenser and thermometer was charged 69.0 grams of wet cake comprising essentially 58% atrazine and 41% water, 960 grams of toluene and 0.20 grams of tris compound. Stirring was begun and the mixture was heated to 60°. When all the solids were dissolved, a small sample of the organic layer was removed. Then 71.0 grams of 1.4% hydrochloric acid solution was charged to the flask. This mixture was held with stirring for 30 minutes at 60°. Stirring was then stopped and a sample of the organic layer was again removed. Both samples were evaporated to dryness and then analyzed for tris content. The sample prior to extraction contained 0.42% tris compound and the sample after extraction contained 0.26% tris compound (38% tris compound removed).

EXAMPLE 7

A slurry of atrazine was prepared by mixing 226.5 grams of wet cake comprising essentially 58% of atrazine and 41% of water, 2496 grams of toluene, 0.66 grams of tris compound, 1.26 grams of sodium hydroxide, 180 grams of sodium chloride and 694.3 grams of water. This mixture was heated to 85°. Thereafter a packed column was filled about the packing level with 1.0% hydrochloric acid. The column was heated to 75° and the flow of the above prepared slurry was started to the column. As it entered the column, the salt water phase mixed with the acid phase in the bottom of the column while the toluene/atrazine phase rose in droplets through the packed section of the column. At the top of the packed section of the column, the toluene/atrazine phase formed a layer over the acid phase and overflowed into the purified atrazine storage. An exit valve for the tris compound extract was then opened and adjusted to maintain the toluene/atrazine-aqueous interface at the desired level. The column was operated in this manner for approximately three hours. Two samples of the purified atrazine/toluene stream were taken in the course of the run. These samples, along with a sample of the original feed stream were evaporated to dryness and analyzed. Operating conditions where the samples were taken and the results obtained are shown in Table I.

Table 1

| Sample | Column Temp. | Ratio Toluene/ Atrazine to HCL Solution | Toluene/ Atrazine Feed Rate (g/min) | % Tris Compound Content | % Tris Compound Removed |
|---|---|---|---|---|---|
| Feed | — | — | — | 0.50 | — |
| A | 75°–81° | 3.4:1 | 8.2 | 0.14 | 72 |
| B | 74°–83° | 3.1:1 | 9.1 | 0.11 | 78 |

EXAMPLE 8

The process of Example 7 was repeated except that 0.4% hydrochloric acid solution was used as the extracting liquid. Operating conditions when the samples were taken and results obtained are shown in Table 2.

Table 2

| Sample | Column Temp. | Ratio Toluene/ Atrazine to HCl Solution | Toluene/ Atrazine Feed Rate (g/min) | % Tris Compound Content | % Tris Compound Removed |
|---|---|---|---|---|---|
| Feed | — | — | — | 0.46 | — |
| A | 77°–78° | 4.2:1 | 8.0 | 0.15 | 67 |
| B | 76°–82° | 4.2:1 | 8.2 | 0.11 | 76 |

EXAMPLE 9

The process of Example 7 was repeated except that 0.1% hydrochloric acid solution was employed as the extracting liquid. Operating conditions when the samples were taken and results obtained, are shown in Table 3.

Table 3

| Sample | Column Temp. | Ratio Toluene/ Atrazine to HCl Solution | Toluene/ Atrazine Feed Rate (g/min) | % Tris Compound Content | % Tris Compound Removed |
|---|---|---|---|---|---|
| Feed | — | — | — | 0.44 | — |
| A | 70.79° | 4.6:1 | 9.4 | 0.09 | 80 |
| B | 77°–79° | 4.7:1 | 9.5 | 0.08 | 82 |

EXAMPLE 10

The process of Example 7 was repeated except that 1% sulfuric acid solution was employed as the extracting liquid. Operating conditions when the samples were taken and results obtained, are shown in Table 4.

Table 4

| Sample | Column Temp. | Ratio Toluene/ Atrazine to HCl Solution | Toluene/ Atrazine Feed Rate (g/min) | % Tris Compound Content | % Tris Compound Removed |
|---|---|---|---|---|---|
| Feed | — | — | — | 0.36 | — |
| A | 75°–78° | 3.0:1 | 7.7 | 0.08 | 78 |
| B | 75°–82° | 2.8:1 | 7.8 | 0.07 | 81 |

EXAMPLE 11

An aqueous atrazine filtrate is adjusted to pH 5.0 using 37% hydrochloric acid. A control sample is submitted for analysis and the remainder is divided into 150 ml aliquots. Then 15 ml aliquots of solvent are added to the filtrate samples and mixed well for one hour at 17° C. The layers are then separated and the aqueous layers are sent for analysis.

| Solvent | Results ppm atrazine | ppm tris compound |
|---|---|---|
| control | 31.3 | 86.2 |
| cyclohexane | 20.4 | 88.2 |
| xylene | 4.2 | 61.0 |
| chlorobenzene | 3.7 | 31.0 |
| ethylene dichloride | 3.5 | 11.4 |

EXAMPLE 12

A large aliquot of an aqueous atrazine filtrate is adjusted to pH 5.4 using 37% hydrochloric acid. A control sample is submitted for analysis. Four 150 ml aliquots are then taken and adjusted to the desired pH. A 15 ml aliquot of toluene is added to each sample which is then well mixed for one hour at 40°–50° C. The layers are then separated and the aqueous layers are sent for analysis.

| pH | Results ppm atrazine | ppm tris compound |
|---|---|---|
| control (5.4) | 34.1 | 77.5 |
| 7.0 | 6.4 | 11.3 |
| 5.4 | 3.4 | 22.8 |
| 3.9 | 1.5 | 51.2 |
| 2.1 | 1.2 | 68.5 |

This data indicates better atrazine extraction and poorer tris compound extraction as the pH drops.

EXAMPLE 13

A large aliquot of an aqueous atrazine filtrate is adjusted to pH 2.0 and divided into five 200 ml aliquots, including a control which is not treated with solvent. Varying amounts of toluene are added to the other four samples which are well mixed for one hour at 40°–50° C. The layers are separated and the aqueous layer is adjusted to pH 5.0 and sent for analysis. The control is also adjusted to pH 5.0 and sent for analysis.

| ml toluene | Results ppm atrazine | ppm tris compound |
|---|---|---|
| control | 28.2 | 77.0 |
| 12 | 2.5 | 74.4 |
| 8 | 5.2 | 71.7 |
| 4 | 9.5 | 80.9 |
| 2 | 12.1 | 73.8 |

This clearly demonstrates the better extractability of atrazine vs. tris compound at lower pH.

What is claimed is:

1. In a process for the production of a chloro-bis(alkylamino)-s-triazine compound having the structural formula

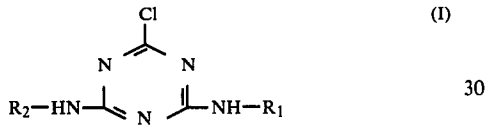 (I)

in which $R_1$ and $R_2$ independently represent lower alkyl of 1 to 4 carbon atoms or cycloalkyl of 3 to 6 carbon atoms, in which a water-immiscible organic process stream is obtained comprising one compound of the formula defined above in a water-immiscible solvent and a tris(alkylamino)-s-triazine by-product of the structural formula

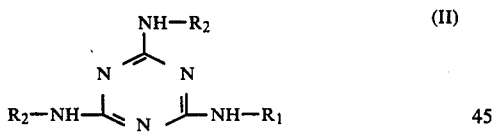 (II)

wherein $R_1$ and $R_2$ have the meaning as defined under structural formula (I) as impurity, the improvement which comprises separating said tris(alkylamino)-s-triazine by-product from said water-immiscible organic process stream by treating said organic process stream with an aqueous acid solution in the pH-range of 5.4 to 0.5 and leaving all of the chloro-bis(alkylamino)-s-triazine product of the structural formula (I) in the organic process stream in a purified state and essentially free of an undesirable compound of the structural formula (II).

2. The process as claimed in claim 1 wherein the extraction treatment is carried out in the form of a batchwise operation.

3. The process as claimed in claim 1 wherein the extraction treatment is carried out in the form of a continuous operation.

4. The process as claimed in claim 1 wherein the organic process stream is obtained in the production of a compound of the structural formula (I) selected from among 2-chloro-4,6-bis(ethylamino)-s-triazine, 2-chloro-4,6-bis(isopropylamino)-s-triazine or 2-chloro-4-ethylamino-6-isopropylamino-s-triazine wherein said immiscible solvent is selected from the group consisting of benzene, toluene and xylene, and wherein an acid is selected from the group consisting of hydrochloric acid, sulfuric acid and phosphoric acid.

5. The process as claimed in claim 1 wherein the organic process stream is obtained in the production of 2-chloro-4-ethylamino-6-isopropylamino-s-triazine wherein the water immiscible solvent is toluene and wherein the acid is hydrochloric acid.

6. The process of claim 1 wherein the tris(alkylamino)-s-triazine compound of the formula (II) is 2,4-bis(ethylamino)-6-isopropylamino-s-triazine.

7. In a process for the production of a chloro-bis(alkylamino)-s-triazine compound having the structural formula

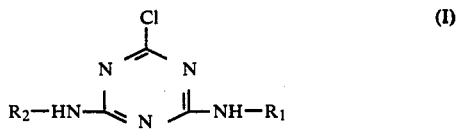 (I)

in which $R_1$ and $R_2$ independently represent lower alkyl of 1 to 4 carbon atoms or cycloalkyl of 3 to 6 carbon atoms, in which an alkaline effluent filtrate is obtained comprising one compound of the formula defined above and a tris(alkylamino)-s-triazine by-product of the structural formula

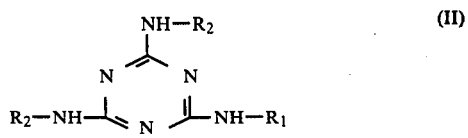 (II)

wherein $R_1$ and $R_2$ have the meanings as defined under structural formula (I) as impurity, the improvement which comprises removing said tris(alkylamino)-s-triazine by-product from said filtrate by treating said filtrate with an agent capable of reducing said alkaline filtrate to a pH-range of 5.4–0.5 and subjecting said acid-adjusted filtrate to an extraction treatment with a water-immiscible solvent to remove a chloro-bis(alkylamino)-s-triazine compound of the formula (I) from said filtrate.

8. The process as claimed in claim 7 wherein an alkaline effluent filtrate is used which is obtained in the production of a compound of the structural formula (I) selected from among 2-chloro-4,6-bis(ethylamino)-s-triazine, 2-chloro-4,6-bis(isopropylamino)-s-triazine or 2-chloro-4-ethylamino-6-isopropylamino-s-triazine and wherein said alkaline effluent filtrate is reduced to a pH-range of 5.4–0.5 by means of hydrochloric acid, sulfuric acid or phosphoric acid and wherein said acid-adjusted filtrate is subjected to an extraction treatment with an aromatic water-immiscible solvent.

9. The process as claimed in claim 7 wherein an alkaline effluent filtrate is used which is obtained in the production of 2-chloro-4-ethylamino-6-isopropylamino-s-triazine and wherein said alkaline effluent filtrate is reduced to a pH-range of 5.4–0.5 by means of hydrochloric acid or sulfuric acid and wherein said acid-adjusted filtrate is subjected to an extraction treatment with toluene.

10. The process of claim 7 wherein the tris(alkylamino)-s-triazine compound of the formula (II) is 2,4-bis(ethylamino)-6-isopropylamino-s-triazine.

* * * * *